United States Patent [19]

Gondouin

[11] Patent Number: 4,761,515

[45] Date of Patent: Aug. 2, 1988

[54] LIQUIFIED NATURAL GAS CONVERSION PROCESS

[75] Inventor: Oliver M. Gondouin, San Rafael, Calif.

[73] Assignee: S-Cal Research, San Rafael, Calif.

[21] Appl. No.: 807,976

[22] Filed: Dec. 12, 1985

Related U.S. Application Data

[63] Continuation-in-part of Ser. No. 688,058, Dec. 31, 1984, Pat. No. 4,705,908.

[51] Int. Cl.⁴ .............................................. C07C 2/00
[52] U.S. Cl. .................... 585/500; 585/300; 585/415; 585/417; 585/541; 585/661; 585/943
[58] Field of Search ............. 585/300, 500, 415, 943, 585/417, 661, 541

[56] References Cited

U.S. PATENT DOCUMENTS

4,350,835  9/1982  Chester et al. ...................... 585/415
4,507,517  3/1985  Devries et al. ...................... 585/500

Primary Examiner—Curtis R. Davis

[57] ABSTRACT

Liquified Natural Gas (L.N.G.) is re-vaporized by heat exchange and pre-heated in a furnace at a temperature not exceeding 1100° C. It is fed, together with an ionized hydrogen plasma stream, into a reactor containing a catalyst of the type described in the co-pending application No. 688,058. After heat exchange with the vaporizing L.N.G., the reactor effluent is separated into a condensed low-vapor-pressure liquid hydrocarbon product, rich in aromatics, into a hydrogen-rich gaseous by-product and into a recycle gas stream. The process is of particular interest where thermal or electrical energy is available at low cost. The Liquified Natural Gas Conversion Process may be considered as a method for storing such energy because the resulting liquid hydrocarbon product can be stored at low cost and may be sold during periods when such energy is in surplus.

17 Claims, 6 Drawing Sheets fig.1 fig.3 fig.4

LIQUIFIED NATURAL GAS CONVERSION PROCESS

The present application is a continuation in-part of the co-pending application Ser. No. 688,058, filed on 12/31/84, now U.S. Pat. No. 4,705,908, entitled "Natural Gas Conversion Process" of which it constitutes a specific application case to Liquefied Natural Gas.

The Liquefied Natural Gas (LNG) (1) is revaporized by heat exchange (2) with the gaseous effluent of a short residence time catalytic reactor (3) and pre-heated in a furnace (4). It is then converted in said reactor, in the presence of a hydrogen stream (5). The liquid hydrocarbon product stream (6), the hydrogen-rich by-product stream (7) and the recycle stream (8) are separated by condensation following heat exchange (9) with the vaporizing LNG.

This process produces a gasoline-like product from LNG and from the use of electricity available at low cost during low consumption periods.

FIELD OF THE INVENTION

The Liquefied Natural Gas (LNG) Conversion Process constitutes a particular case of the more general Natural Gas Conversion Process, subject of the co-pending patent application Ser. No. 688,055.

The LNG composition is that of nearly pure Methane. It is stored at a temperature of about $-260°$ F. Its use as fuel requires re-vaporization by addition of heat from external sources. Due to the low temperature level at which LNG re-vaporization takes place, very little use has been made of the refrigeration potential available from vaporizing LNG. Consequently, the energy of liquefaction is largely unrecovered, which makes LNG an expensive fuel, used primarily for peak-shaving by gas distributor companies. LNG consumption is therefore seasonal, primarily in winter and the costly facilities required for liquefaction, storage and re-vaporization of LN are poorly utilized in summer. LNG conversion into a motor fuel (gasoline and diesel fuel) using the process described therein provides an increased utilisation of presently unused LNG facilities. (Motor fuel consumption peaks in summer). The use of LNG as feed also greatly simplifies the conversion process described in the co-pending patent application Ser. No. 688,055.

Furthermore, this conversion process, which is largely endothermic, may make use of surplus electrical power, also available in summer, to provide an inexpensive source of heat for the pre-heating furnace and for producing the hydrogen plasma required by this process.

Storage of the hydrocarbon liquids resulting from the conversion is rather inexpensive, so that the LNG conversion process, when using electricity as a source of heat, may be considered as a way of indirectly storing surplus electrical power derived in the summer from nuclear plants or from hydroelectric plants.

SUMMARY OF THE INVENTION

Figure 1:
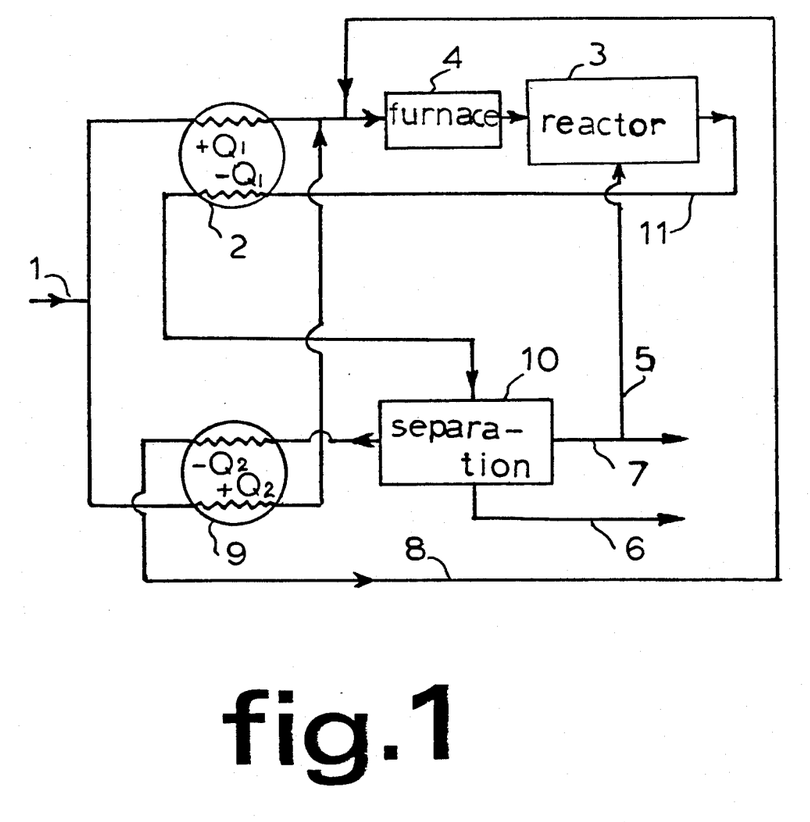
FIG. 1 is a schematic block diagram of the LNG conversion process, derived from FIG. 1 of the co-pending application, and showing the respective flows of LNG, liquid product, hydrogen, and recycle stream, together with the heat exchanges with vaporizing LNG.

The Natural Gas Conversion Process, when applied to a Liquefied Natural Gas (LNG) feed may be greatly simplified as shown on FIG. 1. LNG is practically free of C3 C4 components constituting the Rich Gas stream in the co-pending application. Consequently, some of the units required for Natural Gas conversion may be omitted. These include: the Feed Splitting unit and the Catalytic Reactor, which are without any object when the feed stream is LNG. Steps (a), (b), (c), and (e) of claim 1 of the co-pending application become unnecessary. Furthermore, conversion of a Lean Gas Stream (here re-vaporized LNG) being de-coupled from that of Rich Gas Stream now absent, the residence time in the Short Residence Time reactor may be significantly increased, in which case its operating temperature may increase up to 1100° C., but conventional fixed bed catalytic reactors can then be used instead of the cyclone reactor. The low temperature of vaporization of LNG may also greatly simplify the Separation Unit, which was not described in detail in the co-pending application. Vaporizing LNG is used as cooling medium for the reflux of fractionation columns required for the respective separations of Hydrogen and unreacted Lean Gas streams, thus eliminating the need for any mechanical refrigeration in the Separation Unit.

DETAILED DESCRIPTION OF THE INVENTION

PROCESS DESCRIPTION

Figure 2:
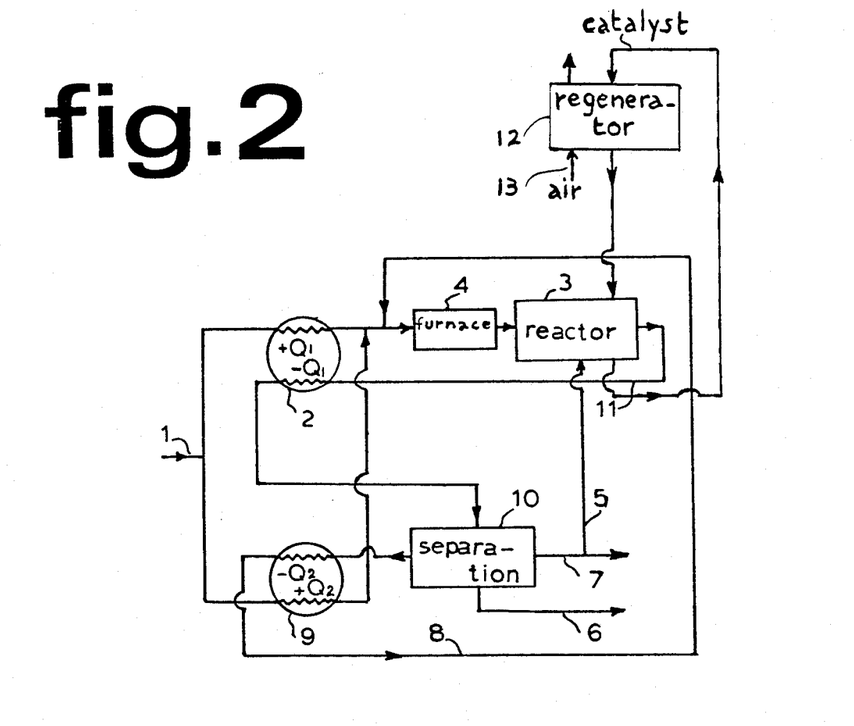
FIG. 2 is a schematic block diagram of the LNG conversion process, including the flow of catalyst and its regeneration in an oxygenated stream. The heat produced in the regenerator may be recovered from the stack gases to provide re-boiler heat for the separation unit.
Figure 3:
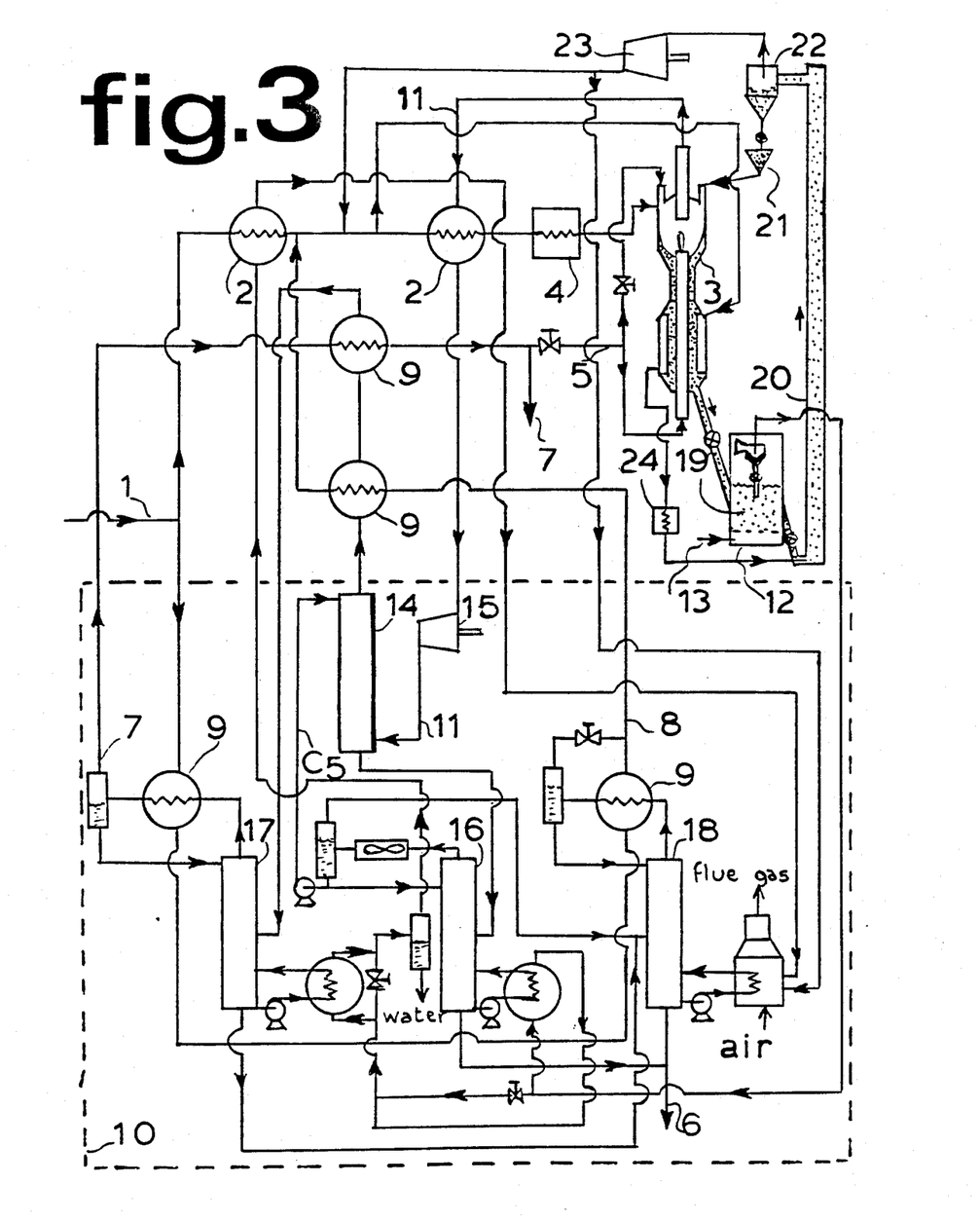
FIG. 3 is a process flow diagram showing an example of application in which a separation unit based on cryogenic fractionation is detailed.

Referring to FIG. 1, the following steps for the conversion of LNG are shown:

The LNG feed stream (1) is re-vaporized in the heat exchangers (2) and (9), mixed with the recycle stream (8), and pre-heated in the furnace (4). The hot gas mixture is then sent to the catalytic reactor (3), which also receives a hydrogen stream (5) where it is converted into an ionized plasma. The reactor effluent stream (11) is chilled in heat exchanger (2) and sent to the separation unit (10). The effluents from the separation unit are respectively: the liquid product stream (6), the recycle stream (8), and the hydrogen by-product stream (7) of which a small side stream (5) is sent to the reactor, the remainder being exported. FIG. 2 adds to the schematic diagram of FIG. 1 the circulation of catalyst, including facilities for its regeneration by combustion of the carbon built-up in an oxygenated stream (13). FIG. 3 shows an example of application in which the heat exchange (2) between LNG and reactor effluent (11) is done first in a gas/gas heat exchanger, followed by solvent extraction of Benzene from the effluent, and second in a LNG vaporizer.

The separation unit is limited by a dotted line box on the flow diagram of FIG. 3. It includes, in addition to the Benzene extraction column (14) a compressor (15) and 3 distillation columns (16), (17) and (18), producing respectively the solvent (C5), hydrogen (7), the recycle stream (8) and the liquid product (6). The actual disposition of the separation unit is not limited to this example nor to the use of distillation columns. Adsorption columns may also be used and their disposition is well known to those skilled in the art. In the example of FIG. 3, the reactor is a cyclone reactor (3), of the type described in the co-pending application and catalyst regeneration is by means of a fluidized bed (19) in the regenerator (12).

In the example of FIG. 3, catalyst transport against gravity from the regenerator (12) to the reactor (3) is by means of a lift column using re-vaporized LNG as lift gas. The fresh catalyst is stored in a hopper (21) while the lift gas is separated in a cyclone (22) recompressed by a compressor (23) and recycled to the reactor inlet. A portion of the separated lift gas (22) may also be used as fuel for the reboilers of the fractionation columns (16), (17), and (18). A furnace (24) preferably electric heats the lift gas so as to maintain the catalyst temperature at a high level (up to 900° C.) prior to its introduction into the reactor (3).

Figure 4:
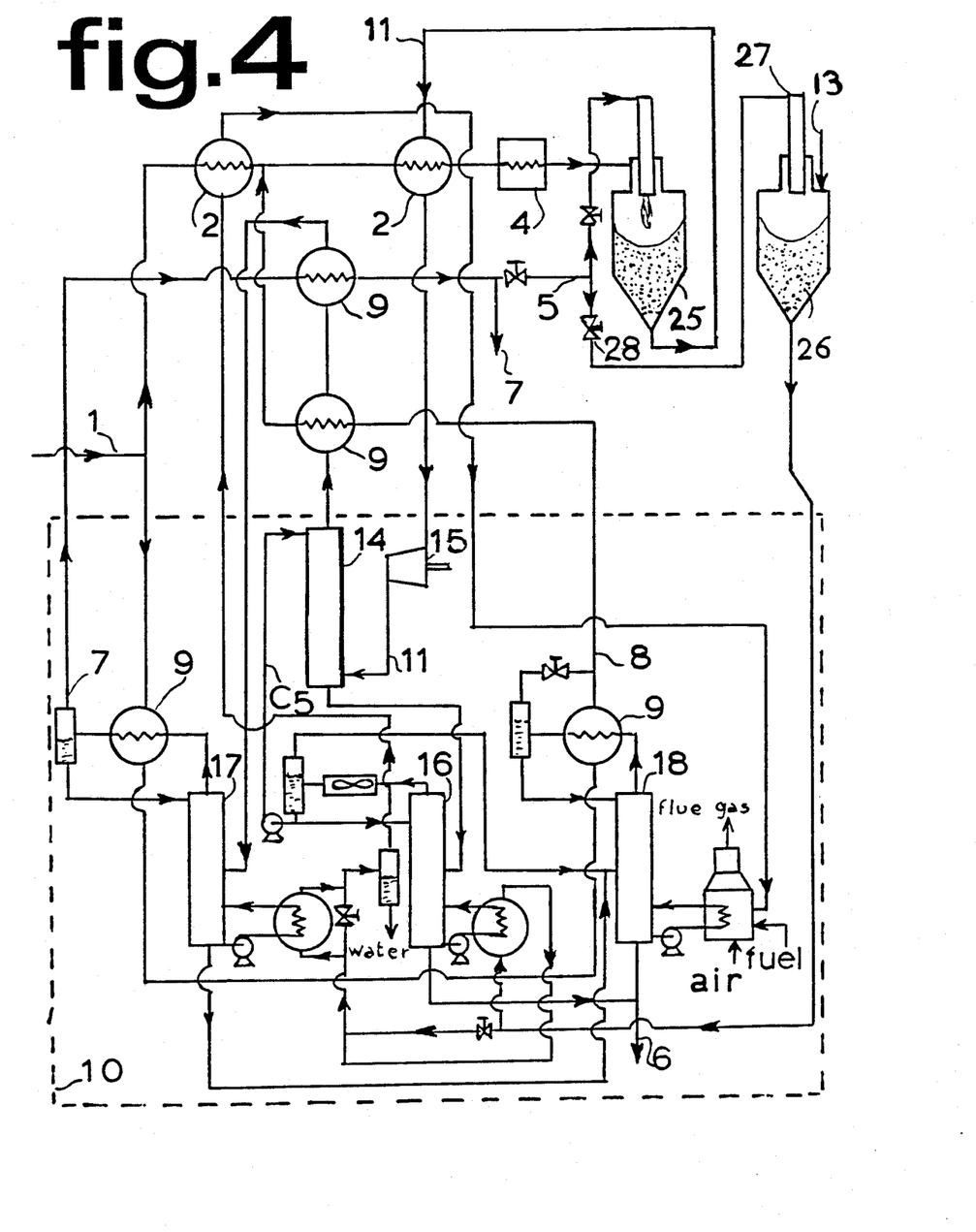
FIG. 4 is a process flow diagram showing an example of application in which the cyclone reactor, with a longer residence time and higher operating temperature.

Because this process is simpler than that of FIG. 4 of the co-pending application, a plurality of fixed bed catalytic reactors (25) may be used in lieu of the cyclone reactors and fluidized bed regenerator. This is shown on FIG. 4. One of 2 reactors (26) is subjected to a regeneration cycle while the other reactors are operated in the conversion mode. During the regeneration cycle, the plasma torch (27) is switched off and the hydrogen flow is interrupted by closing the hydrogen feed valve (28). The residence time in a fixed bed reactor is significantly greater (up to 0.5 sec.) than in a cyclone reactor. To maintain the carbon selectivity at low level, the hydrogen flow is increased (up to 20% of the Methane flow), and the spent catalyst temperature is also increased up to 1100° C. Suitable manifolds and valves, (not shown on FIG. 4), are used to successively rotate each fixed-bed reactor from the conversion mode to the regeneration mode. This type of operation is well known of those skilled in the art.

Figure 5:
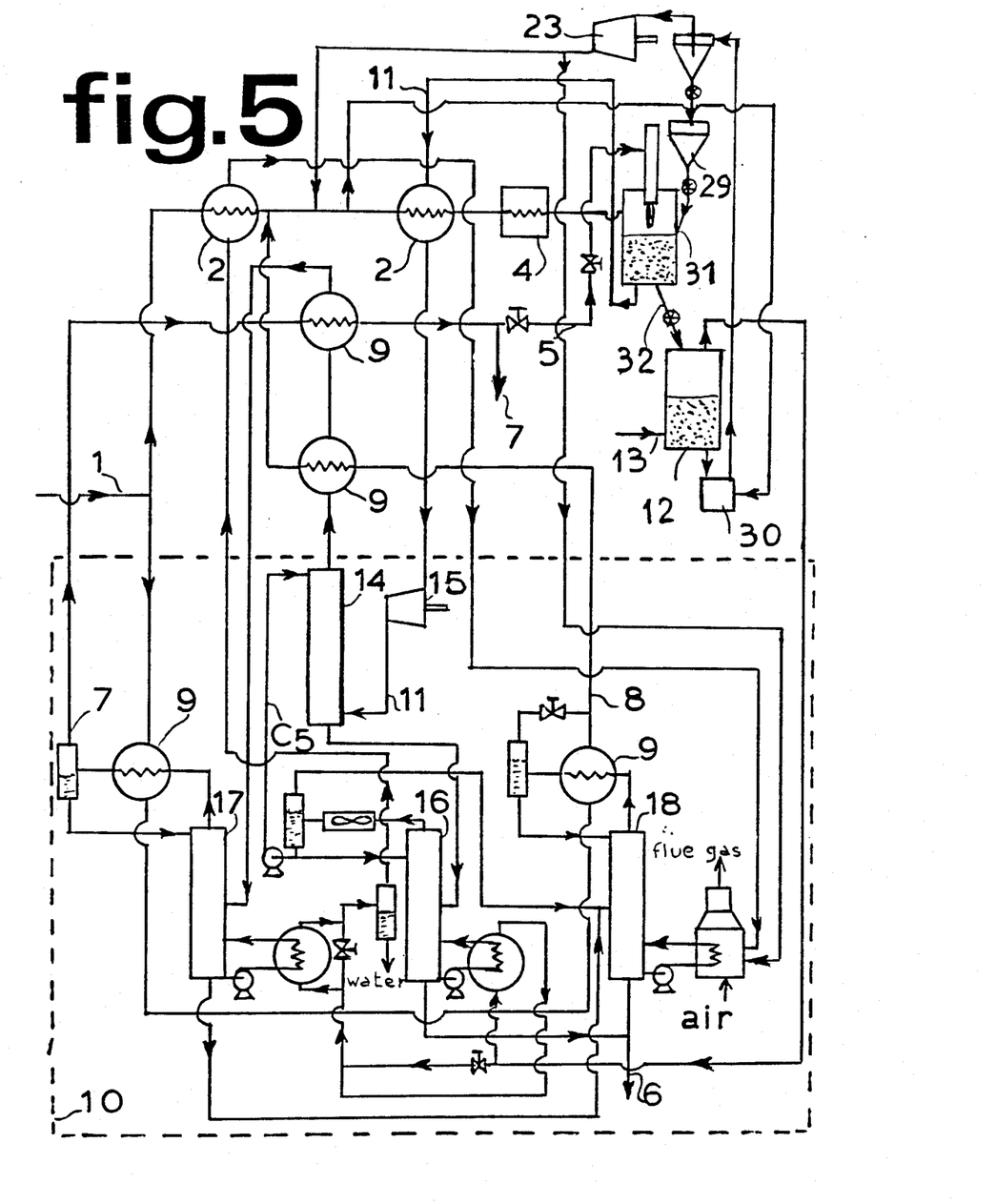
FIG. 5 is a process flow diagram showing an example of application in which both the reactor and the regenerator are of the moving bed type.

FIG. 5 shows an example of application in which the catalytic reactor is of the moving-bed type. A continuous flow of catalyst, by gravity, is established between the reactor and the regenerator. The fresh catalyst is continuously lifted to the feed hopper (29) by means of a lift pot (30) in which the lift gas is some revaporized LNG heated to a temperature of about 600° C.

EXAMPLES

The catalyst is prepared from a solution in Ethanol of Thorium nitrate, Lanthanum nitrate, Gallium nitrate, and Zirconium nitrate, as described above. Co-precipitation from the solution, buffered with Diethanolamine, is achieved wtih a Benzoic acid solution in Ethanol. The precipitate, after separation, washing, drying, and calcination, yields a mixed oxide crystal characterized by the following X-ray diffraction spectrum (using a 20 KV source, 1.54059 wave length Cu K alpha-2):

| Angstroms* | Line intensity (count per second above background) |
|---|---|
| 19.72 | weak (with diffractometer run at 3°/m) |
| 8.74 | Weak |
| 5.05 | very weak |
| 3.74 | weak |
| 3.22 | very strong |
| 2.78 | strong |
| 1.97 | strong |
| 1.69 | strong |
| 1.39 | weak |
| 1.28 | medium |
| 1.13 | medium |
| 1.07 | weak |

*Interplanar spacing

Figure 6:
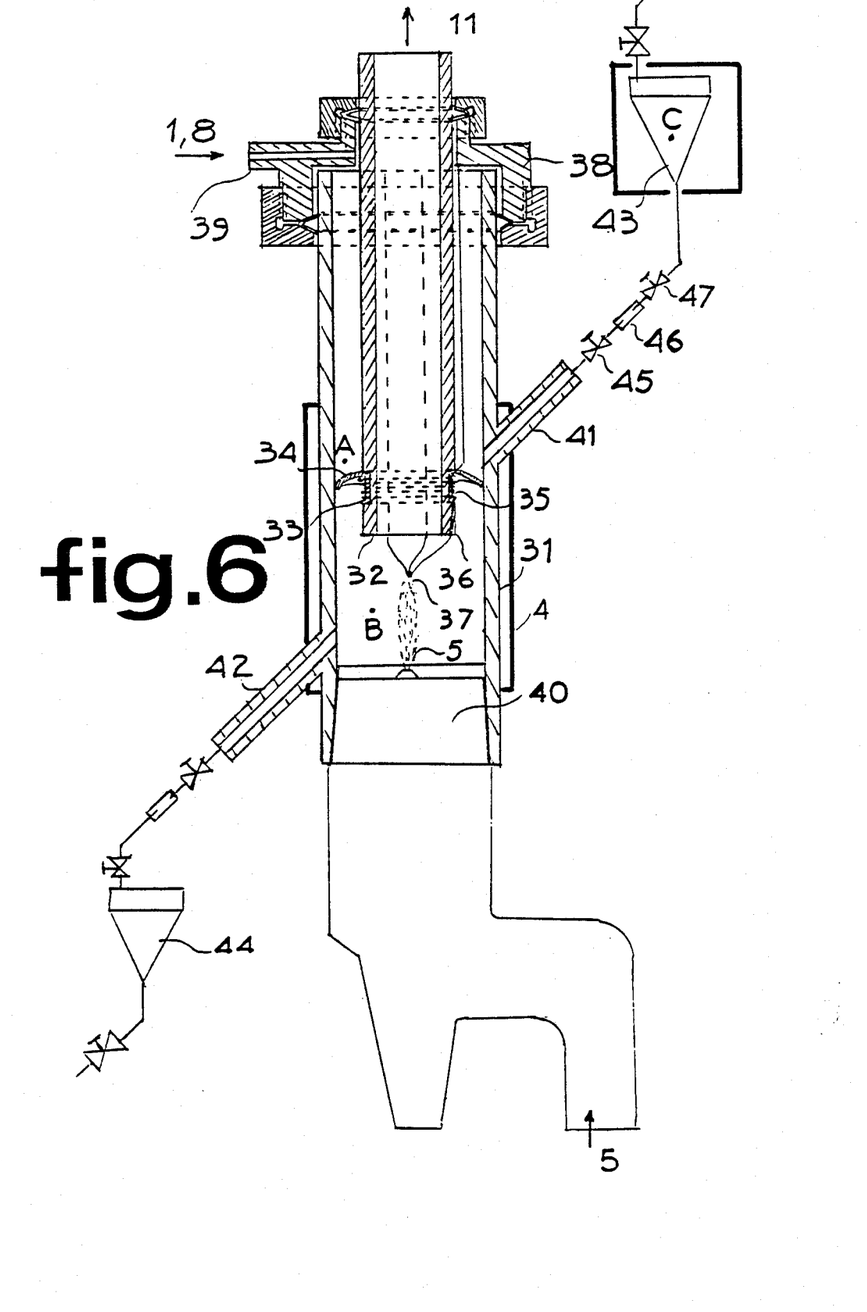
FIG. 6 is a vertical cross section of a laboratory apparatus used to demonstrate the effects of the catalyst and of the hydrogen plasma on the conversion of Methane-rich feeds in a cyclone reactor, and of Propane-rich feeds in a fluidized bed reactor.

The catalyst is ground in a mortar. Only the fraction comprised between 100 mesh and 230 mesh is retained for the tests. The cyclone reactor configuration shown on FIG. 6 is essentially that of FIG. 8 of the co-pending application, wherein the cylindrical cavity is made from a fused quartz tube (31) of $\frac{3}{4}''$ ID and 20'' long oriented vertically. The gaseous effluent from the reactor is carried through a $\frac{7}{8}''$ OD, $\frac{5}{8}''$ ID alumina tube (32), 18'' long, concentric with the quartz tube. A circular groove (33), 1/32'' deep and $\frac{1}{4}''$ wide is cut by abrasion into the outer surface of the alumina tube (32), $\frac{1}{2}''$ from its end. A $\frac{3}{4}''$ diameter disk (34) cut from a No. 6 gauge Platinum foil is cut at six equidistant locations along its periphery over a $\frac{1}{8}''$ radial distance and the 6 blades thus formed are twisted into helicoidal vanes. Similarly, 6 radial cuts are made, bisecting the inner part of each helicoidal vane from the center of the disk to a radial distance of $\frac{1}{4}''$. Each of the resulting triangular blades is bent at 90° and the lower part of the alumina tube is pushed into the resulting hexagonal opening, until the bent triangular blades fit snugly into the circular groove of the alumina tube. The shaped Platinum piece is held firmly in place by wrapping over the triangular blades 6 loops of 10 gauge Tungsten wire (35). The lower ends of the 6 wires pass through the slits between the Platinum vanes and are gathered below to form a bird-cage configuration pressing against the lower end of the alumina tube. The apex of the bird-cage (37), with all 6 wires welded together, is centered along the axis of the tube. The upper end of each wire is pulled to about 1'' from the other end of the alumina tube and attached to a stainless steel connection cap (38), closely fitted around the alumina tube (32). The assembly is then inserted into the quartz tube (31), with the connecting cap covering the quartz tube upper end in a gas-tight fit. The connecting cap also includes a tangential pipe connection (39) through which the pre-heated feed gas is injected. The stainless steel piece (38) is electrically grounded. The bottom end of the fused quartz tube (31) is machined by grinding to tightly mate with the conical part of the ceramic shroud (40) of a commercial plasma torch (Secheron Microplasma MP 5-21). The distance between the apex of the Tungsten wire bird-cage (37) and the noozle of the plasma torch is adjusted so that the transferred arc from the torch to the Tungsten wires remains stable under normal operating conditions of the microplasma torch (100 to 10,000 Hz pulse rate, Hydrogen flow rate 1 to 5 l/m, transferred arc current 0.1 to 5 amp.)

Two short lateral quartz tubes, (41), (42), $\frac{1}{8}''$ ID, are fused into the side of the main quartz tube, oriented at an angle of 30° towards each end respectively. these tubes are used for catalyst injection into, and removal from the main quartz tube. Each tube is connected to a stainless steel hopper (43) (44) by means of a block valve (45) in series with a threaded joint (46) and a regulating valve (47). The top branch tube (41) is connected to the bottom of the catalyst feed hopper, and the bottom branch tube to the top of the receiving hopper. The boundaries of the cyclone reactor chamber are respectively at the top the Platinum helicoidal vanes (34), and at the bottom the ceramic shroud (40) of the Microplasma torch. The catalyst is injected just above the Platinum vanes and is removed at a level just above the ground joint of the quartz tube. The effective volume of the reactor chamber thus formed is 11 cc. Electrical heating coils are wrapped respectively around the main quartz tube and around the top catalyst hopper.

The temperature is measured at three points by means of quartz-sheathed Pt-Rh thermocouples:
a. in the quartz-alumina annular spaceabove the catalyst injection point, (feed gas temperature)
b. in the reactor chamber at a radial distance of ¼" from the axis, and ½" below the end of the alumina tube,
c. within the catalyst feed hopper (catalyst temperature) Pressure is measured at the inlet gas feed line.

The reactor effluent flowing through the top end of the alumina tube is divided into two streams, the main one exhausting to the atmosphere outside after passing through an oil-filled trap, and the minor one sent to a gas chromatograph for on-line analysis of the conversion products.

The electrical power W applied to the plasma torch, after correction for heat losses to the torch cooling water, is also measured.

Average volume flow rates of feed gas F, hydrogen H, at standard conditions, and the mass flow rate C of catalyst are recorded for each test.

Table 1 summarizes some typical results for pure Methane (tests 1, 2, and 3), representative of LNG. These are compared wtih test 4 for a C1, C2 mixture representative of the Lean Gas fraction of a Natural Gas, as described in the co-pending application.

TABLE 1

| Test N° | 1 | 2 | 3 | 4 |
|---|---|---|---|---|
| $T_A$ (°C.) | 890 | 890 | 895 | 890 |
| $T_B$ (°C.) | 860 | 1050 | 890 | 1050 |
| $T_C$ (°C.) | 600 | 600 | N.A. | 600 |
| P (psia) | 20 | 20 | 20 | 20 |
| W (watts) | 0 | 340 | 0 | 350 |
| F (l/m) | 30 | 30 | 30 | 29 |
| H (l/m) | 5 | 3 | 3 | 3 |
| C (g/m) | 10 | 10 | 0 | 10 |
| Feed Comp. (volume %) | 100% C1 | 100% C1 | 100% C1 | 93% C1, 7% C2 |
| Results (Average for 10 minutes runs) | | | | |
| % weight conversion | 5 | 37 | 1 | 45 |
| % liquid selectivity | 55 | 64 | 25 | 66 |

Carbon selectivity is very low in all cases. By-product gas is mostly hydrogen in all cases. Liquids produced are rich in Aromatics.

At the end of each ten minutes run, the catalyst feed hopper is almost empty and the receiving hopper is nearly full. All the valves are closed on the two lines connecting the two hoppers to the cyclone reactor, and the threaded joints between each pair of valves are disassembled. The feed hopper is interchanged for the receiving hopper. The threaded joints are reassembled and thermocouple C is inserted into the hopper located in the heating furnace. The system is ready for another run when the catalyst temperature measured by this thermocouple has stabilized. The four valves on the catalyst flow path are opened and a new run of the cyclone reactor begins.

The conversion of pure Methane is also compared wtih that of Propane, representative of the Rich Gas fraction of Natural Gas as described in the co-pending application. In a separate series of experiments, the bottom line of the feed hopper is disconnected from the cyclone reactor and connected to a Propane cylinder. The top outlet of the same hopper is connected to the gas chromatograph and to the gas disposal line. The Propane mass flow rate is derived from weight loss of the cylinder. For a catalyst temperature of 600° C. and a Propane flow rate of 2 g/m, corresponding to a residence time of 6 seconds, the Propane conversion is 52%, with a liquid selectivity of 71%. At the end of a 10 minutes conversion run, the Propane flow is replaced by a Nitrogen flow, followed by an air flow period, resulting in the combustion of the carbon built up. From a measurement of the CO2 produced in the combustion, the carbon built up is estimated at less than 2% of the total carbon in the Propane feed during the preceding conversion run.

With the laboratory apparatus shown on FIG. 6, the electrostatic potential of the Tungsten wires (37) may also be adjusted to a value different from that of electrical ground. For this purpose, a Platinum foil is wrapped around the inner surface of the quartz tube (31), and connected to the electrical ground of the plasma torch. An electrostatic generator (not shown on FIG. 6), also connected to this common ground, maintains the electrostatic potential of the Tungsten wires, (37), and of the Platinum vanes (34), at a negative value of at least 500 volts. With the plasma torch Tungsten tip maintained at a positive voltage, with respect to the common ground, the plasma jet length may be increased. Under these conditions, it is also observed that, at constant electrical power W of the plasma torch, the Methane conversion yield is increased. This increase in yield is attributed to the increase in probability of collision between ions generated in the gas phase with adsorbed molecules on the catalyst.

I claim:

1. A process for the conversion of the paraffinic hydrocarbon components of Liquified Natural Gas (LNG), of carbon number 1 or 2, into an aromatics-rich liquid mixture of hydrocarbons having a number of carbon atoms greater than 3, and into a hydrogen-rich gaseous by-product, said process comprising the following steps;
    (a) revaporization into a gaseous phase of LNG in heat exchangers receiving the hot gaseous effluents from a short residence time catalytic reactor wherein the catalyst consists essentially of actinide and lanthanide elements in combustion with gallium and zirconium,
    (b) pre-heating of said gaseous phase stream, and of the recycled gas stream in a furnace,
    (c) reaction between an ionized hydrogen plasma and the mixture of the preheated gas stream of LNG and the recycled gas stream, in the presence of a catalyst in a short residence time reactor, (d) separation of the solid particles of said catalyst from the stream of gaseous products of said reactor, (e) removal of hydrogen and light hydrocarbons products of carbon number less than 3 from said gaseous product stream in a separation unit utilizing as cooling fluids low temperature streams derived from LNG, (f) recyclling said recycled gas stream of light hydrocarbons to said furnace and reactor, and (g) regeneration of said catalyst by combustion of the coke deposited on said catalyst, with an oxidizing stream.

2. A process according to claim 1 wherein the pre-heated gas stream of LNG and the recycled gas stream is pre-heated to a temperature not exceeding 1100° C.

3. A process according to claim 1 wherein said short residence time reactor is a cyclone reactor comprising:
(a) an upper part having a vertical cylindrical cavity equipped with at least:
an inlet by which said pre-heated lean gas stream is injected and set into rotational flow,
a vertical peripheral inlet from which said catalyst flows into the tangential flow of said pre-heated lean gas,
(b) along its vertical axis, an ionized hydrogen plasma jet stream,
(c) a hydrogen-cooled heat shield made of refractory materials, protecting the upper part of said cyclone reactor from the heat radiated by said hydrogen plasma,
(d) a plurality of secondary hydrogen cooling streams and means for injecting them into said cylindrical cavity and for setting them into rotational flows, with the direction of at least one said rotating hydrogen steam opposite to that of said lean gas stream, and
(e) in its lower part, a co-axial conical cavity with a bottom outlet from which the spent catalyst flows while exchanging heat with said rich gas stream in a heat recovery section of the reactor located below said conical cavity.

4. The process according to claim 1 wherein said short residence time reactor is a fixed bed catalytic reactor having at least one outlet for the gaseous product stream and at least two inlets respectively for the pre-heated gaseous mixture of streams and and for a jet of ionized hydrogen plasma.

5. The process according to claim 1 wherein said short residence time reactor is a moving bed catalytic reactor presenting the same number of openings at least one outlet for the gaseous product stream and at least two inlets for the preheated gaseous mixture of streams of LNG and recycled gas stream, plus one additional outlet for the spent catalyst, and one additional inlet for the fresh catalyst flowing by gravity.

6. The process according to claim 1 above characterized by the fact that said separation unit (10) includes a compressor, a solvent extraction column (14), and at least 3 fractionation columns of which at least two fractionation columns are equipped with reflux condensers cooled by a vaporizing or vaporized LNG stream.

7. The process according to claim 1 wherein the catalyst particles are electrically charged at a negative potential with respect to that of the cylindrical wall of said cyclone reactor, before their entry into the cylindrical cavity of said reactor.

8. The process of claim 1 wherein the catalyst consists essentially of a crystalline form of refractory mixed oxides of composition:

$$x\ MO_2,\ y\ M'M''O_3,\ z\ M'''O_2$$

wherein x, y and z are mole fractions with value comprised between 0.5% and 98%, and where
M is an actinide metal,
M' is a lanthanide metal,
M" is gallium,
M'" is zirconium,
and where x is greater than y, and y is greater than z.

9. The process of claim 8 wherein said crystalline form of refractory mixed oxides is obtained by:
(a) forming a precipitate from a water and alcohol solution of soluble salts of metals M M'M"M'" buffered with an organic base, using as a precipitation reagent a solution in water and alcohol of a heat-decomposable acid,
(b) heating the washed precipitate in an autoclave in the presence of steam,
(c) air drying the resulting crystals,
(d) compacting said air dried crystal into pellets,
(e) heating said pellets in an inert atmosphere at a temperature exceeding the decomposition temperature of said acid, and
(f) sintering said pellets at 1000° in presence of steam.

10. The process of claim 9 wherein said precipitation reagent is a solution is water and alcohol of a salt of said heat-decomposable acid in which the cations belong to a class which includes all alkali metals and ammonium.

11. The process of claim 9 wherein:
(a) said heat-decomposable acid belongs to a class selected from benzoic acid, oxalic acid, carbonic acid or mixtures thereof;
(b) said organic base used to buffer said solution belongs to a group selected from pyridine, alcohol diamines, alkane diamines of carbon number equal to or greater than 3, or quaternary ammonium salts.

12. The process of claim 1, wherein the temperature of said catalytic bed reactor does not exceed 600° C. and the residence time exceeds 3 seconds.

13. The process of claim 3 wherein the top surface of said cyclone reactor is conical, with an internal angle from the horizontal at least equal to the angle of repose of said catalyst pellets.

14. The process of claim 13 wherein the inner top conical surface of said cyclone reactor and the back face of said heat shield are cooled by cold secondary hydrogen streams also injected into said cyclone reactor top at several points above the periphery of said heat shield and guided along spiral trajectories towards a central annular collector from which said secondary hydrogen streams flow first downward through openings in said heat shield, along spiral trajectories around the vertical axis of said plasma stream.

15. The process of claim 3 wherein the angular direction of rotation of the trajectories of at least one of said secondary hydrogen streams is opposite to that of the vortex formed by the catalyst and lean gas stream injected into said cyclone reactor, so that turbulent mixing occurs.

16. The process of claim 3 wherein said spent catalyst is regenerated by combustion of the residual carbon on said catalyst with a mixture of oxygen, nitrogen and steam.

17. The process of claim 16 wherein the catalyst regeneration is obtained at temperatures not exceeding 600° C.

* * * * *